United States Patent [19]

Taylor

[11] Patent Number: Plant 7,248

[45] Date of Patent: Jun. 19, 1990

[54] PEACH 'ITO RED'

[75] Inventor: James W. Taylor, Dinuba, Calif.

[73] Assignee: Ito Packing Co., Inc., Reedley, Calif.

[21] Appl. No.: 306,753

[22] Filed: Feb. 6, 1989

[51] Int. Cl.[5] ..... A01H 5/00

[52] U.S. Cl. ..... Plt./43

[58] Field of Search ..... Plt. 43

*Primary Examiner*—James R. Feyrer

*Attorney, Agent, or Firm*—Dennis B. Haase

[57] ABSTRACT

A new and distinct variety of peach tree characterized by yellow fleshed fruit of the cling stone type and having a maturity period in the latter part of the season, at which time the fruit will have good sugar content and a large size with a rose red base color and a deeper red colored stipules. The pit is freely removed with very few fibers attached and the sum cavity is very small.

1 Drawing Sheet

BACKGROUND OF THE VARIETY

The present invention relates to a new and distinct variety of peach tree, which I refer to as Ito Red, of a yellow fleshed, cling stone fruit, attractive in appearance, maturing in the late season period, which was developed from a continued fruit breeding program.

ORIGIN AND ASEXUAL REPRODUCTION OF THE NEW VARIETY

This novel peach was derived from an ongoing fruit breeding program for the improvement of peaches and nectarines to enhance quality and market acceptability. The flowers of the Red Jim variety (U.S. Plant Pat. No. 4,518) were emasculated and pollenated with pollen from an unnamed variety of late peach. Seeds produced from this method were stratified and grown to a height of about 18 inches. These seedlings were bud grafted into dehorned flame kissed nectarine host in the experimental orchard of Ito Packing Co., Inc., Reedley, Calif., for testing and selection. Each clone was budded into several limbs to make sure that it propagated true to type.

SUMMARY OF THE VARIETY

The instant variety developed through the above method was selected because of its excellent eating quality, its red, slightly mottled blush which extends almost entirely over a yellow ground color and late season of maturity.

BRIEF DESCRIPTION OF THE DRAWINGS

The accompanying drawing illustrates typical specimens of the fruit and foliage of my new variety as grown in the San Joaquin Valley of California. Two specimens are shown, one of which is in the side elevation and the other from the apex view; yet another specimn is a section side elevation illustrating the internal texture and color of the flesh and pit.

DETAILED DESCRIPTION

The following is a detailed description of my new variety with color reference being to the Maerz and Paul Dictionary of Colors, except in instances where terminology having generally accepted meaning is employed.

Parentage: Red Jim × Unnamed peach selection.

Propagation: Maintains its distinguishing characteristics through several bud grafts.

Locality where grown and observed: Near Reedley, County of Fresno, Calif.

TREE

Size: Large, vigorous; upright, open, vase form, productive.

Trunk: Medium size; medium texture.

Leaves:

- *Average length.*—5.3 inches; average width 1.4 inches; medium thickness.
- *Color.*—Top side — 32B10; underside 31I8.
- *Margin.*—Glandular; crenate.
- *Petiole.*—Medium length; medium thickness.
- *Glands.*—Average number — two to three.
- *Position.*—Usually two on at the base of the leaf blade near the attachment of the petiole but occasionally three; often two on the petiole near the leaf blade, one being on either side of the petiole.
- *Type.*—Reniform, small, but frequently being globose in shape.

Flower bud: Medium size.

Flowers: Large, showy.

- *Color.*—Pink.
- *Date of full bloom.*—With variety Red Jim (U.S. Plant Pat. No. 4,518).

Anthers: Red.

FRUIT

Maturity:

- *When described.*—Firm ripe — Aug. 25, 1988.

Date of first picking: Aug. 25, 1988

Date of last picking: Sept. 15, 1988

Size

- *Average axial length.*—3.0 inches; average transverse width in suture plane — 3.2 inches.
- *Uniformity.*—Generally uniform other than halves often being unequal to the left or right of the suture plane.

Form: Essentially round but compressed at the base. Often slightly larger on left half but may be larger on half to the right of the ventral suture.

- *Suture.*—Shallow, deepens slightly at the apex leaving the point usually below the contour of the fruit. Dorsal suture present but very shallow except near the apex where it deepens slightly to meet ventral suture. The apex is usually pressed slightly toward one side of the suture, usually away from the enlarged cheek.

Ventral surface: Characteristically protruding toward the ventral suture.

Cavity: Round, deep, depth from ½ to ⅝ inch; very small stem attachment area with stem fitting very tightly into cavity area.

Base: Flattened, slightly.

Apex: Smooth with slight point; usually recessed with the suture.

Skin:

*Thickess.*—Medium texture; peels readily.

*Tendency to crack.*—None observed.

*Bloom.*—Wanting.

*Color.*—Yellow ground color nearly totally covered with a moderate to heavy, mottled rose to red blush.

*Down or hairiness.*—Fuzzy, very short.

*Texture.*—Very firm, meaty.

*Color.*—Deep yellow (10L3) with some red (5E6) splashed into the flesh. Very close to the pit there is a very dark red area (55L12) that darkens to a very dark red right at the pit (56A12).

*Juice.*—Abundant.

*Amygdalin.*—Not present in flavor.

*Flavor.*—Good balance of acid and sugar. Very sweet. Retains good flavor during long storage period.

*Aroma.*—Quite pronounced for yellow fleshed peach.

*Fibers.*—Very few fibers attached to the pit causing the pit to separate easily from the fruit. When eaten out of hand, there is very little flesh attached to pit in comparison to the large amount of flesh left around the pit with other cling varieties.

*Eating quality.*—Excellent.

Stone:

*Adherence to flesh.*—Cling stone but with few fibers attached to the stone when fully mature.

*Size.*—Small, average thickness 0.7 inches; average width 0.7 inches; average length 1.2 inches.

*Form.*—Oval.

*Hilum.*—Very small, nearly round in comparison to other peach pit hilums which are usually oblong.

*Dorsal edge.*—Very narrow with shallow groove.

*Ventral edge.*—Very narrow with no wing toward apex.

*Surface.*—Irregular small grooves and pits.

*Color.*—Brown (7L12) shaded to reddish brown throughout (47L1).

*Tendency to split.*—Very little.

Use: Fresh market.

Keeping quality: Excellent.

Shipping quality: Excellent.

Resistance to disease: Similar to other glanded varieties of peaches.

Although this novel variety of peach tree possesses the described characteristics as a result of the growing conditions in the Reedley area of Fresno County, Calif., in the central portion of the San Joaquin Valley, it is to be understood that variations of the usual magnitude in characteristics incident to growing conditions, fertilization, pruning and pest control are to be expected.

Having thus described and illustrated my new peach tree, what is new and desired to be secured by Letters Patent is:

1. A new and distinct variety of peach tree with fruit of yellow fleshed cling stone type, substantially as herein shown and described, having a maturity period in the late season, having fruit of good sugar content, the fruit being large with a rose red base color and deep red color stipules over much of the exterior with very small stem cavity and very few fibers attached to the pit.

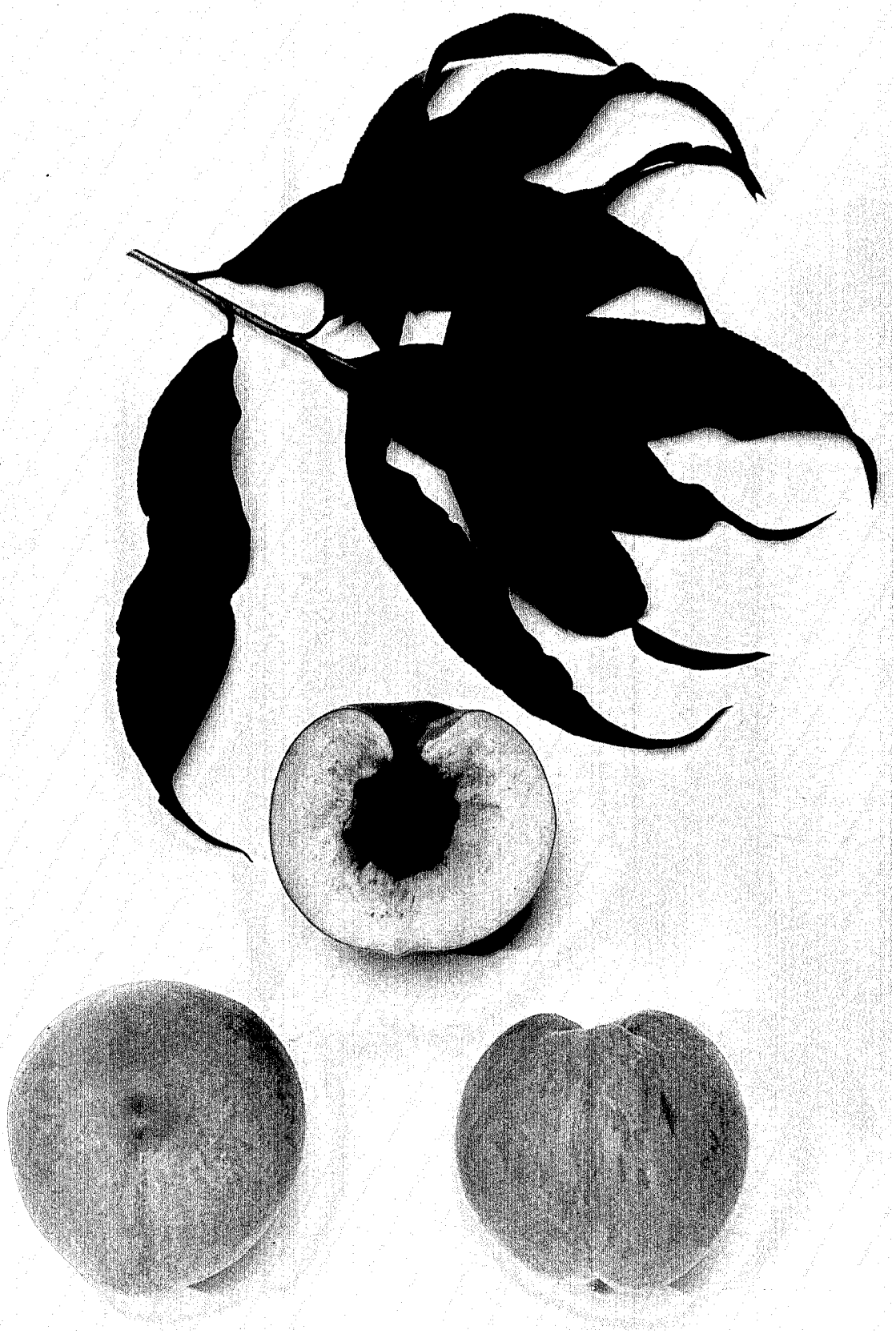

* * * * *